| United States Patent [19] | [11] | 4,212,796 |
|---|---|---|
| König | [45] | Jul. 15, 1980 |

[54] PROCESS FOR THE PREPARATION OF CYSTEINE-CONTAINING PEPTIDES

[75] Inventor: Wolfgang König, Hofheim am Taunus, Fed. Rep. of Germany

[73] Assignee: Hoechst Aktiengesellschaft, Frankfurt am Main, Fed. Rep. of Germany

[21] Appl. No.: 2,347

[22] Filed: Jan. 10, 1979

[30] Foreign Application Priority Data

Jan. 12, 1978 [DE] Fed. Rep. of Germany ....... 2801175

[51] Int. Cl.$^2$ ...................... C07C 103/52; C07G 7/00
[52] U.S. Cl. ...................... 260/112.5 R; 260/112.5 S; 260/112.5 T; 260/112.5 TR
[58] Field of Search ............... 260/112.5 R, 112.5 S, 260/112.5 T

[56] References Cited

U.S. PATENT DOCUMENTS

| 3,875,136 | 4/1975 | Kamber | 260/112.5 R |
|---|---|---|---|
| 3,910,872 | 11/1975 | Riniker et al. | 260/112.5 T |
| 4,038,306 | 8/1977 | Milkowski et al. | 260/112.5 R |
| 4,111,924 | 9/1978 | Fujino et al. | 260/112.5 T |

*Primary Examiner*—Delbert R. Phillips
*Assistant Examiner*—Blondel Hazel
*Attorney, Agent, or Firm*—Curtis, Morris & Safford

[57] ABSTRACT

A process for the preparation of cysteine-containing peptides by detachment of the S-trityl groups by means of trifluoroacetic acid, wherein S-trityl compounds of these peptides are treated with a mixture of a mercaptan and trifluoroacetic acid.

3 Claims, No Drawings

PROCESS FOR THE PREPARATION OF CYSTEINE-CONTAINING PEPTIDES

In the synthesis of cysteine-containing peptides, the trityl radical has become increasingly important for protecting the mercapto function. However, the acid detachment of this protective group met with difficulties in the case of higher-molecular peptides. Thus, the protective groups could only be detached from an insulin-A chain, wherein the 4-cysteine groups were protected by trityl groups, by means of repeated treatments with HBr and trifluoroacetic acid or HF, compare Z. Naturforsch. 24 b, 1128 (1969). The yield of insulin-A chain tetrasulfonates in the case of a fully protected chain was only 21%.

Pure trifluoroacetic acid causes no detachment (Chem. Ber. 101, 681 (1968)); however, after the trifluoroacetic acid solution of the S-trityl compound had been poured into water, 70–75% detachment was observable in the case of H-Cys(Trt)-OH. In the case of peptides, however, the proportion of detachment was at most 60% (J. Chem. Soc. (C) 1970, 2683).

For the above reasons, the S-trityl group in cysteine-containing peptides is in most cases detached by iodine oxidation in organic solvents (J. Chem. Soc. 74 (1952), 1862; Helv. Chim. Acta 51 (1968), 2061) or in aqueous acetic acid (German Auslegeschrift 1,917,939). This oxidation directly produces the corresponding cystine derivative, and deblocking, with regeneration of the mercapto group is thus not possible by this method. A further disadvantage of this method is that iodine, being a powerful oxidizing agent, can form by-products in the case of oxidation-sensitive peptides.

While mixtures of trifluoroacetic acid with water or with the cation acceptor anisole have an adverse influence on the detachment of the S-trityl group, it has been found, surprisingly, that mixtures of trifluoroacetic acid with mercaptans are an excellent and mild medium for detaching S-trityl groups.

The invention relates to a process for the preparation of cysteine-containing peptides by detaching the S-trityl groups by means of trifluoroacetic acid, wherein S-trityl compounds of these peptides are treated with a mixture of a mercaptan and trifluoroacetic acid.

Suitable mercaptans include both aliphatic and aromatic mercaptans, such as, for example, ethylmercaptan, mercaptoacetic acid or thiophenol. Ethylmercaptan has proved particularly advantageous, since it is very volatile and can readily be removed with ether. Preferably, mixtures which contain about 100 moles or more of mercaptan per mole of substance to be deblocked are used.

The trifluoroacetic acid concentration should be at least 30% but should preferably not fall below 40–50%. The reaction time for detaching the trityl groups is about 10–60 minutes, in most cases about 30 minutes, in the case of a 50% strength trifluoroacetic acid/ethylmercaptan solution. The mixture is advantageously worked up by introducing it into water. After introduction into excess water, the peptide is isolated, depending on its solubility, either by filtration or by freeze-drying of the aqueous phase which has been extracted with ether.

The peptide which has been freed from the protective groups can also be isolated by precipitation in organic solvents, such as, for example, diethyl ether, diisopropyl ether or ethyl acetate. This method of working up is used advantageously if the peptides formed are sparingly water-soluble. Any protective groups which may be present and which are easily detachable under acid conditions, which may be present, such as, for example, the 3,5-dimethoxy-$\alpha,\alpha$-dimethylbenzyloxycarbonyl (Ddz) radical, the Boc radical or tert.-butyl ester and ether groups, are also detached in the process according to the invention.

Depending on the nature of these protective groups, the reaction time has to be extended to a greater or lesser degree. For complete detachment of the protective groups of the tert.-butyl type, it is necessary to allow, for example, about 4 hours in a 50% strength trifluoroacetic acid/ethylmercaptan solution. In the case of longer peptides, with several unprotected mercapto groups, repetition of the deblocking treatment may be advantageous.

The reaction by-product formed is, for example, S-tritylmercaptoethane in the case of the detachment of trityl groups by means of trifluoroacetic acid/ethylmercaptan, and passes into the organic phase during working up.

The process according to the invention is particularly valuable in the case of higher peptides, where deblocking by means of iodine is no longer possible for reasons of solubility or for reasons of sensitivity to oxidation. Peptides which are only sparingly soluble in methanol or aqueous acetic acid will still dissolve extremely easily in the trifluoroacetic acid/mercaptan mixtures according to the invention.

Thus, for example, it has proved possible to obtain a synthesized protected human insulin-A chain in yields of about 70% by two treatments with mercaptoethanol/trifluoroacetic acid removing the 4-S-trityl radicals and for the 7-tert.-butyl protective groups. This free reduced insulin-A chain was characterized by converting it to the tetrasulfonate. The product formed was identical with natural human insulin-A chain both in acid electrophoresis and in a thin layer chromatogram.

The cysteine-containing peptides obtained can either be employed directly for therapeutic purposes, as in the case of, for example, Somatostatin for the treatment of pancreatitis, or are used to synthesize higher, therapeutically valuable, peptides.

EXAMPLE 1:

(a) H-Cys-Asn-OH trifluoroacetate ($a_1$) 5.34 g (10 mmoles) of H-Cys(Trt)-Asn-OBu$^t$ (Helv. Chim. Acta 54, 398 (1971)) are added, with stirring, to a mixture of 25 ml of ethylmercaptan and 25 ml of trifluoroacetic acid. The mixture is stirred for 4 hours at room temperature and is then introduced into 250 ml of water. The batch is then extracted three times with ether and the aqueous phase is freeze-dried. Yield 3.271 g (89%).

$[\alpha]_D^{23} = +3.0°$ (c=1, in methanol).

$C_7H_{13}N_3O_4S \cdot CF_3COOH \cdot H_2O$ (367.3) Calculated C 29.40; H 4.39; N 11.44; S 8.73; H$_2$O 4.9. Found 30.5; 4.0; 11.2; 8.9; 4.6.

($a_2$) 1.6 g (3 mmoles) of H-Cys(Trt)-Asn-OBu$^t$ are added, with stirring, to a mixture of 7.5 ml of ethylmercaptan and 7.5 ml of trifluoroacetic acid. The mixture is left to stand for 4 hours at room temperature and is then poured into 50 ml of diisopropyl ether. The precipitate is filtered off, washed with diisopropyl ether and dried. Yield 1 g (91%). $[\alpha]_D^{24} = +3.6°$ (c=1, in water).

In a thin layer chromatogram, the substance is identical with that obtained under a₁).

(a₃) Batch analogous to Example a₂. Diethyl ether is used instead of diisopropyl ether. Yield 0.95 g (86%). $[\alpha]_D^{23} = +3°$ (c=1, in water).

In a thin layer chromatogram, the substance is identical with that obtained under a₁.

(a₄) 533.7 mg (1 mmole) of H-Cys(Trt)-Asn-OBu$^t$ are added, with stirring, to a mixture of 3.7 ml of mercaptoacetic acid and 3.7 ml of trifluoroacetic acid. The mixture is stirred for 4 hours at room temperature and is then poured into 50 ml of diethyl ether. The precipitate is filtered off and washed with diethyl ether.

Yield 210 mg (57%). $[\alpha]_D^{22} = 2.9°$ (c=1, in water).

(b) (H-Cys-Asn-OH)₂ (iodine oxidation of H-Cys-Asn-OH)

2.6 g (7 mmoles) of H-Cys-Asn-OH.CF₃COOH.H₂O are dissolved in 25 ml of 40 percent strength acetic acid and titrated with 0.1 N iodine solution in acetic acid. 67.8 ml of iodine solution are consumed (=97% of theory).

The mixture is then concentrated. The residue is dissolved in water and the aqueous solution is extracted by shaking with ether. The aqueous phase is freeze-dried. Yield 2.42 g (97.6%).

$C_7H_{12}N_3O_4S.0.8$ HI.H₂O (354.6) Calculated C 23.71; H 4.20; N 11.85; S 9.04; I 28.63. Found 24.1; 4.1; 10.5; 8.6; 28.4.

500 mg of the substance obtained above were dissolved in a small amount of water and chromatographed on Amberlite IR 45 (acetate form) 25×1.5 cm). The eluate is freeze-dried.

Yield 260.04 mg (67% of theory, relative to nonoxidized material). $[\alpha]_D^{25} = -62.1°$ (c=1, in water).

$C_7H_{12}N_3O_4S.0.25$ CH₃COOH.H₂O (268.3) Calculated C 33.57; H 6.01; N 15.66; acetic acid 5.59; H₂O 6.71. Found C 34.6; H 5.7; N 16.0; acetic acid 5.7; H₂O 6.9.

EXAMPLE 2:

(a) H-Leu-Glu-Asn-Tyr-Cys-Asn-OH trifluoroacetate 639.8 mg (0.5 mmole) of H-Leu-Glu(OBu$^t$)-Asn-Tyr(Bu$^t$)-Cys-(Trt)-Asn-OBu$^t$.CF₃COOH are dissolved in a mixture of 2.5 ml of ethylmercaptan and 2.5 ml of trifluoroacetic acid. The reaction mixture is stirred for 4 hours at room temperature and is then poured into 50 ml of water. The aqueous phase is extracted three times with ether and is then freeze-dried. Yield 331.5 mg (73%), $[\alpha]_D^{24} = -30.4°$ (c=1, in water).

$C_{31}H_{46}N_8O_{12}S.CF_3COOH.2$ H₂O (904.9) Calculated C 43.80; H 5.45; N 12.38; S 3.54. Found 44.4; 5.6; 12.3; 3.8.

(b) Preparation of the starting substance
H-Leu-Glu(OBu$^t$)-Asn-Tyr(Bu$^t$)-Cys(Trt)-Asn-OBu$^t$ trifluoroacetate (b₁) Ddz-Leu-OTcp 33.3 g of Ddz-Leu-OH (Ann. Chem. 1973, 1652-1662) (94.3 mmoles) and 19.6 g (0.1 mole) of 2,4,5-trichlorophenol are dissolved in 350 ml of ethyl acetate. A solution of 20.4 g of DCC in 60 ml of ethyl acetate is added at 0° C. The mixture is stirred for 3 hours at 0° and overnight at room temperature. The dicyclohexylurea which has precipitated is filtered off and the filtrate is concentrated. The residue crystallizes on standing with petroleum ether overnight in a refrigerator. Yield 39.2 g (73.6%, based on H-Leu-OMe.HCl).

Melting point 108°, $[\alpha]_D^{29} = -31.3°$ (c=1, in dimethylacetamide).

$C_{24}H_{28}NO_6Cl_3$ (532.83) Calculated: C 54.10; H 5.30; N 2.62; Cl 20.01. Found: 54.7; 5.4; 2.9; 19.3.

(b₂) Ddz-Leu-Glu(OBu$^t$)-Asn-Tyr(Bu$^t$)-OH.0.5 H₂O 27.7 g (50 mmoles) of H-Glu(OBu$^t$)-Asn-Tyr(Bu$^t$)-OH (Chem. Ber. 110, 1-11 (1977)) are suspended in 150 ml of dimethylformamide. After adding 6.75 g of HOBt (50 mmoles), solution occurs. The mixture is cooled to 0° C. and 6.5 ml (50 mmoles) of N-ethylmorpholine and 28 g (52.5 mmoles) of Ddz-Leu-OTcp are added. The batch is stirred for 1 hour at 0° C. and 3 hours at room temperature. A Fluoram sample shows that not all of the amino component has as yet reacted. A further 1.3 g of Ddz-Leu-OTcp (2.5 mmoles) are now added and the mixture is allowed to react for several hours at room temperature. If the batch gives a negative Fluoram test, it is worked up. The solvent is distilled off in a high vacuum and the residue is dissolved in ethyl acetate. The solution is brought to pH 4 with ice-cold citrate buffer (pH 3). The ethyl acetate phase is then washed once with citrate buffer (pH 4) and twice with water. It is dried over Na₂SO₄ and concentrated. The residue is triturated with a 1:1 mixture of ether and petroleum ether. The mixture is placed in a refrigerator for several hours and the product is then filtered off.

Yield 35.35 g (80.25%), melting point 222°-223°, $[\alpha]_D^{25} = -23.7°$ (c=1, in methanol).

$C_{44}H_{65}N_5O_{13}.0.5$ H₂O (881.04) Calculated C 60.00; H 7.55; N 7.95. Found 60.0; 7.6; 8.0.

(b₃)
Ddz-Leu-Glu(OBu$^t$)-Asn-Tyr(Bu$^t$)-Cys(Trt)-Asn-OBu$^t$

A solution, cooled to 0° C., of 6.6 g of DCC in 20 ml of dimethylformamide is added to a solution, cooled to 0° C., of 26.4 g (30 mmoles) of Ddz-Leu-Glu(OBu$^t$)-Asn-Tyr(Bu$^t$)-OH hemihydrate, 16.0 g (30 mmoles) of H-Cys(Trt)-Asn-OBu$^t$ and 4.05 g (30 mmoles) of HOBt in 60 ml of dimethylformamide. The batch is stirred for 2 hours at 0° C. and overnight at room temperature. The dicyclohexylurea is filtered off and washed with 20 ml of dimethylformamide. The filtrate is carefully poured into about 250 ml of cooled NaHCO₃ solution, while stirring, and the mixture is extracted with 600 ml of ethyl acetate. The ethyl acetate phase is successively extracted by shaking once with 300 ml of NaHCO₃ solution, once with 300 ml of citrate buffer (pH 4) and once with 100 ml of NaHCO₃ solution, and is dried over Na₂SO₄ and concentrated. The residue is triturated with ether.

Yield 28-34 g (67-81%). Melting point 161°-165°, $[\alpha]_D^{23} = -13.1°$ (c=1, in CH₂Cl₂)

$C_{74}H_{98}N_8O_{16}S$ (1387.73) Calculated: C 64.05; H 7.12; N 8.07; S 2.31. Found: 63.8; 7.3; 8.0; 2.7.

(b₄)
H-Leu-Glu(OBu$^t$)-Asn-Tyr(Bu$^t$)-Cys(Trt)-Asn-OBu$^t$ trifluoroacetate 27.75 g (10 mmoles) of Ddz-Leu-Glu(OBu$^t$)-Asn-Tyr-(Bu$^t$)-Cys(Trt)-Asn-OBu$^t$ are introduced, at room temperature, into a mixture of 17.5 ml of trifluoroacetic acid (0.2 mole), 3.5 ml of water and 330 ml of methylene chloride (=about 350 ml of a 5% strength solution of trifluoroacetic acid in methylene chloride, containing 1% of water). The mixture is stirred for 2 hours at room temperature. It is then cooled to 0° C., the trifluoroacetic acid is neutralized with 17.75 ml (220 mmoles) of pyridine and the mixture is concentrated in vacuo. The residue is dissolved in 250 ml of ethyl acetate and is extracted by shaking 3 times with 25 ml of water. The ethyl acetate phase is concentrated without prior drying. The residue is dried in a high vacuum and then triturated with ether (instead of diethyl ether, diisopropyl ether can also be used). The precipitate is filtered off, washed with ether and dried. Yield 25.2 g. For further purification, about 6 g portions in 30 ml of ethyl acetate are heated to the boiling and centrifuged off while warm. The precipitates are then each stirred twice with ether, centrifuged off and dried in a high vacuum over $P_2O_5$. Yield 22.3 g (86%).

Melting point 178°–182°, 161°–164°, 166°–171°, $[\alpha]_D^{22} = -3.5$ to $+4.0°$ (c=1, in 90 percent strength acetic acid).

$C_{64}H_{85}N_8O_{14}SF_3$ (1279.5) Calculated: C 60.08; H 6.70; N 8.76; S 2.51. Found: 59.4; 6.5; 9.1; 2.9.

Amino acid analysis: Asp (2.0), Glu (1.05), Cys (0.87), Leu (0.99), Tyr (1.05)

EXAMPLE 3:

(a) H-Tyr-Gln-Leu-Glu-Asn-Tyr-Cys-Asn-OH trifluoroacetate 814 mg (0.5 mmole) of H-Tyr(Bu$^t$)-Gln-Leu-Glu(OBu$^t$)-Asn-Tyr(Bu$^t$)-Cys(Trt)-Asn-OBu$^t$ trifluoroacetate are dissolved in a mixture of 5 ml of ethylmercaptan and 5 ml of trifluoroacetic acid. The reaction mixture is left to stand for 4 hours at room temperature and is then poured into 50 ml of water. The aqueous phase is extracted three times with ether and is freeze-dried.

Yield 590 mg (98%). $[\alpha]_D^{25} = -15.3°$ (c=1, in 90 percent strength acetic acid).

$C_{45}H_{63}N_{11}O_{16}S \cdot CF_3COOH \cdot 2\ H_2O$ (1196.2) Calculated: C 47.19; H 5.73; N 12.88; S 2.68. Found: 47.0; 5.6; 12.0; 3.0.

(b) Preparation of the starting substance H-Tyr(Bu$^t$)-Gln-Leu-Glu(OBu$^t$)-Asn-Tyr(Bu$^t$)-Cys(Trt)-Asn-OBu$^t$ trifluoroacetate (b$_1$) H-Tyr(Bu$^t$)-OMe.HCl 300 g (778 mmoles) of Z-Tyr(Bu$^t$)-OMe (Ann. Chem. 696, 226 (1966)) are dissolved in 1 liter of methanol and hydrogenated catalytically (Pd/BaSO$_4$ catalyst) at pH 4.5, using an auto-burette (about 2 N methanolic HCl being added). After completion of hydrogenation, the catalyst is filtered off and the filtrate is concentrated. The residue is triturated with ether.

Yield 189.2 g (84.5%)

Melting point 154°–156°, $[\alpha]_D^{22} = +15.0°$ (c=1, in methanol)

$C_{14}H_{22}NO_3Cl$ (287.79) Calculated: C 58.43; H 7.7; N 4.86. Found: 58.6; 7.6; 4.8.

(b$_2$) Ddz-Tyr(Bu$^t$)-OMe 35 ml (0.25 mole) of triethylamine and 79.5 g (0.3 mole) of Ddz azide are added to a solution of 71.95 g (0.25 mole) of H-Tyr(Bu$^t$)-OMe. HCl in 110 ml of dimethylformamide while cooling with ice and stirring. After 5 minutes, a further 35 ml (0.25 mole) of triethylamine are added. The icebath is then removed and the mixture is allowed to come to room temperature. After 30 minutes, 7 ml (50 mmoles) of triethylamine are added and the mixture is stirred for 3 hours at room temperature. The batch is left to stand overnight at room temperature and is then partitioned between 250 ml of ethyl acetate and 250 ml of water. After adding ice, the ethyl acetate phase is washed 3 times with 125 ml of ice-cold citrate buffer (pH 3) at a time, once with 250 ml of saturated NaHCO$_3$ solution and once with 125 ml of water, dried over Na$_2$SO$_4$ and concentrated. It is then dried under a high vacuum. Yield 118.2 g of an oil (99.8%).

(b$_3$) Ddz-Tyr(Bu$^t$)-OH

The 118.2 g (249.5 mmole) of oily Ddz-Tyr(Bu$^t$)-OMe obtained under 2) are dissolved in 500 ml of 1,2-dimethoxyethane and a pinch of thymolphthalein is added. 250 ml of 1 N NaOH are added dropwise, whilst stirring. The mixture is stirred until the blue color of the batch has faded. A further 120 ml of 1 N NaOH are now added gradually, in several portions, until the solution no longer loses its color (the additional consumption of sodium hydroxide solution is due to the ethyl acetate content of the starting material). The mixture is then neutralized with citric acid and the solution is concentrated. Ice water is added to the residue and the mixture is brought to pH 3.5 with citric acid at 0° C. The resulting oil is taken up in ethyl acetate. The ethyl acetate phase is extracted by shaking twice with 200 ml of citrate buffer (pH 4) and twice with 200 ml of water. The ethyl acetate phase is dried over Na$_2$SO$_4$, the ethyl acetate is distilled off and the residue is dried under a high vacuum. A yellowish white amorphous substance remains.

Yield 99.5 g (86.8%)

Melting point about 38°–40°, $[\alpha]_D^{22} = +41.5°$, (c=1, in methylene chloride).

$C_{25}H_{33}NO_7$ (459.55) Calculated: C 65.34; H 7.24; N 3.05. Found: 65.0; 7.3; 3.0.

(b$_4$) Ddz-Tyr(Bu$^t$)-Gln-ONb 6.4 ml (50 mmoles) of N-ethylmorpholine and 10.5 g of DCC are added at $-3°$ C. to a solution of 25.24 g (55 mmoles) of Ddz-Tyr(Bu$^t$)-OH, 15.88 g (50 mmoles) of H-Gln-ONb.HCl (Chem. Ber. 110, 1–11 (1977)) and 6.75 g of HOBt monohydrate in 100 ml of dimethylformamide. The mixture is stirred for 1 hour at 0° C. and 6 hours at room temperature and is then left to stand overnight at room temperature. The precipitate is filtered off and the filtrate is concentrated. The resulting oil is dissolved in ethyl acetate and the solution is washed successively with NaHCO$_3$ solution, citrate buffer (pH 3) and water, dried over Na$_2$SO$_4$ and concentrated. The oil is triturated with petroleum ether under it is reduced to a powder, and is filtered off. For further purification, the substance is boiled three times with 100 ml of diisopropyl ether at a time and the ether is decanted off in each case. Finally, the substance is triturated with cold diisopropyl ether, filtered off and rinsed with petroleum ether.

Yield 32.8 g (91%), melting point 80°–90°, $[\alpha]_D^{22} = +15.1°$ (c=1, in methanol)

$C_{37}H_{46}N_4O_{11}$ (722.81) Calculated: C 61.48; H 6.41; N 7.75. Found: 61.3; 6.7; 7.9.

(b$_5$) Ddz-Tyr(Bu$^t$)-Gln-OH-DCHA 5 ml of water and a Pd/BaSO$_4$ catalyst are added to a solution of 32.5 g (45 mmoles) of Ddz-Tyr(Bu$^t$)-Gln-ONb in 500 ml of methanol and the substance is hydrogenated for 7 hours. The catalyst is then filtered off and the filtrate is concentrated. The oil which remains is dissolved in 250 ml of ethyl acetate. 11.3 ml (55 mmoles)

of dicyclohexylamine are added. The mixture is left to stand for a few hours in a refrigerator and the precipitate is filtered off. The filter residue is triturated with ethyl acetate in a mortar, filtered off and dried in vacuo.

Yield 27 g (78%)

Melting point 170°–171°, $[\alpha]_D^{23} = +10.2°$ (c=1, in methanol)

$C_{42}H_{64}N_4O_9$ (769.0) Calculated: C 65.6; H 8.39; N 7.28. Found: 65.4; 8.5; 7.3.

(b₆) Ddz-Tyr(Buᵗ)-Gln-OH 2.9 g (3.77 mmoles) of Ddz-Tyr(Buᵗ)-Gln-OH.DCHA are partitioned between ethyl acetate and citrate buffer (pH 3). The ethyl acetate phase is washed neutral with water, dried over $Na_2SO_4$ and concentrated. An amorphous product remains.

Yield 2 g (90%)

Melting point 110°–115°, $[\alpha]_D^{22} = +19.8°$ (c=1, in methanol)

$C_{30}H_{41}N_3O_9$ (587.68) Calculated: C 61.31; H 7.03; N 7.15. Found: 60.6; 7.2; 7.0.

(b₇)
Ddz-Tyr(Buᵗ)-Gln-Leu-Glu(OBuᵗ)-Asn-Tyr(Buᵗ)-Cys(Trt)-Asn-OBuᵗ

9.7 g (16.5 mmoles) of Ddz-Tyr(Buᵗ)-Gln-OH, 19.2 g (15 mmoles) of H-Leu-Glu(OBuᵗ)-Asn-Tyr(Buᵗ)-Cys(Trt)-Asn-OBuᵗ.CF₃COOH and 2.025 g (15 mmoles) of HOBt are dissolved in 30 ml of dimethylformamide at room temperature, while stirring. The mixture is then cooled to 0° C. and 1.95 ml (15 mmoles) of N-ethylmorpholine and a solution of 3.3 g (16 mmoles) of DCC in 9 ml of dimethylformamide are added. The mixture is stirred for 1 hour at 0° C. and 4 hours at room temperature and is then left to stand overnight at room temperature, after which the dicyclohexylurea is filtered off. The filter residue is washed twice with 4.5 ml of dimethylformamide at a time. The filtrate is run into 159 ml of saturated NaHCO₃ solution, whilst stirring, and the mixture is stirred until a pulverulent precipitate is formed. The precipitate is filtered off, triturated with citrate buffer (pH 3), filtered off and washed neutral with water. It is dried in a high vacuum.

Yield 23.1 g.

The crude substance is heated almost to the boiling on a steam bath. The thin suspension is placed in a refrigerator overnight and the precipitate is filtered off and washed with ethyl acetate and ether.

Yield 20 g (76.8%)

$[\alpha]_D^{24} = -10.2°$ (c=1, in methanol). The suspension decomposes from 205° onwards and chars at about 250°.

$C_{92}H_{123}N_{11}O_{20}S$ (1735.15)

| Amino acid analysis: | Asp | Glu | Cys | Leu | Tyr |
|---|---|---|---|---|---|
| Calculated: | 2.0 | 2.0 | 1.0 | 1.0 | 2.0 |
| Found: | 2.00 | 2.01 | 0.75 | 0.99 | 1.95 |

(b₈)
H-Tyr(Buᵗ)-Gln-Leu-Glu(OBuᵗ)-Asn-Tyr(Buᵗ)-Cys(Trt)-Asn-OBuᵗ trifluoroacetate 3.5 g (2 mmoles) of Ddz-Tyr(Buᵗ)-Gln-Leu-Glu(Obuᵗ)-Asn-Tyr(Buᵗ)-Cys(Trt)-Asn-OBuᵗ are dissolved in a mixture of 1.75 ml of trifluoroacetic acid (20 mmoles), 0.35 ml of water and 33 ml of methylene chloride (=about 35 ml of a 5% strength solution of trifluoroacetic acid, containing 1% of water) and 3.5 ml of anisole, while stirring.

The mixture is stirred for 3 hours at room temperature, 2 ml (24.8 mmoles) of pyridine are then added, and the batch is concentrated in a high vacuum. The residue is triturated with ether, filtered off, washed with water and dried over P₂O₅.

Yield 3.35 g.

For further purification, the substance was briefly heated to boiling with 20 ml of ethyl acetate at a time, and was filtered off hot. It was then rinsed with ether.

Yield 3.0 g (92%), melting point 255°–265° (with decomposition), $[\alpha]_D^{24} = -23.8°$ (c=1, in methanol).

$C_{80}H_{109}N_{11}O_{16}S.CF_3COOH$ (1626.9)

| Amino acid analysis: | Asp | Glu | Cys | Leu | Tyr |
|---|---|---|---|---|---|
| Calculated: | 2 | 2 | 1 | 1 | 2 |
| Found: | 1.95 | 2.08 | 0.81 | 1.07 | 2.04 |

EXAMPLE 4:

(a) H-Cys-Ser-Leu-OH trifluoroacetate 564 mg (0.97 mmole) of H-Cys(Trt)-Ser-Leu-OH.H₂O (Chem. Ber. 103, 2034 (1970)) are dissolved in a mixture of 2.5 ml of ethylmercaptan and 2.5 ml of trifluoroacetic acid. The mixture is left to stand for 30 minutes at room temperature and the batch is poured into 50 ml of water. The aqueous phase is extracted three times with ether and is freeze-dried.

Yield 331 mg (78%)

$[\alpha]_D^{28} = -15.4°$ (c=1, in methanol)

$C_{12}H_{21}N_3O_4S.CF_3COOH.H_2O$ (435.4)

Calculated: C 38.62; H 5.56; N 6.95. Found: 38.7; 6.0; 9.4.

The same result as above is obtained if 564 mg of H-Cys(Trt)Ser-Leu-OH.H₂O are deblocked in a mixture of 11 ml of trifluoroacetic acid and 11 ml of thiophenol (the conditions otherwise being as above).

EXAMPLE 5:

(a) H-Ile-Cys-Ser-Leu-OH trifluoroacetate 677 mg (0.91 mmole) of H-Ile-Cys(Trt)-Ser-Leu-OH.0.3 CF₃COOH.1.5 H₂O are dissolved in a mixture of 2.5 ml of ethylmercaptan and 2.5 ml of trifluoroacetic acid. The reaction mixture is stirred for 30 minutes at room temperature and is then poured into 50 ml of water, while stirring. The aqueous phase is extracted three times with ether and is then freeze-dried.

Yield 506 mg (98%)

$[\alpha]_D^{24} = -11.3°$ (c=1, in methanol).

$C_{18}H_{34}N_4O_6S.CF_3COOH.H_2O$ (566.6) Calculated: C 42.39; H 6.58; N 9.89. Found: 42.4; 7.0; 10.6.

(b) Preparation of the starting substance H-Ile-Cys(Trt)-Ser-Leu-OH (b₁) Ddz-Ile-OTcp A cold solution of 52 g (252 mmoles) of DCC in 175 ml of ethyl acetate is added to a solution, cooled to 0° C., of 87 g (246 mmoles) of Ddz-Ile-OH (Ann. Chem. 763, 162–172 (1972)) and 48.6 g (246 mmoles) of 2,4,5-trichlorophenol in 700 ml of ethyl acetate. The mixture is stirred for 3 hours at 0° C. and is then left to stand at room temperature overnight. The dicyclohexylurea is filtered off and the filtrate is concentrated in vacuo. The residue crystallizes when treated with petroleum ether.

Yield 105.6 g (80.5%).

Melting point 92°-94°, $[\alpha]_D^{22} = -22.6°$ (c=1, in methanol).

$C_{24}H_{28}NO_6Cl_3$ (532.86) Calculated: C 54.10; H 5.30; N 2.63; Cl 19.96. Found: 54.4; 5.4; 2.8; 19.5.

(b₂) Ddz-Ile-Cys(Trt)-Ser-Leu-OH.1 H₂O 63.95 g (120 mmoles) of Ddz-Ile-OTcp are added, at room temperature, to a solution of 69.8 g (120 mmoles) of H-Cys(Trt)-Ser-Leu-OH monohydrate (Chem. Ber. 103, 2034-2040 (1970)) and 16.2 g (120 mmoles) of HOBt in 300 ml of dimethylformamide, after which the mixture is stirred for 4 hours at room temperature. A further 5.33 g (10 mmoles) of Ddz-Ile-OTcp are then added if there is still tripeptide present. The mixture is left to stand overnight at room temperature and the solvent is distilled off in vacuo. The oil which remains is partitioned between 400 ml of ethyl acetate and 250 ml of saturated sodium carbonate solution, whereupon the sodium salt of the Ddz-tetrapeptide remains in the ethyl acetate. The ethyl acetate phase is cooled and is successively extracted by shaking with about 120 ml of 1 N citric acid solution (after the extraction the aqueous phase should have a pH of about 3-4), 150 ml of citrate buffer (pH 3) and twice 200 ml of water. The ethyl acetate phase is then dried over $Na_2SO_4$ and concentrated in vacuo. The residue is triturated with petroleum ether and filtered off.

Yield 99.8 g (90%).

Melting point (130) 135°-140° (with decomposition). $[\alpha]_D^{22} = -34.1°$ (c=1, in methanol).

$C_{49}H_{62}N_4O_{10}S.1 H_2O$ (917.1)

Calculated: C 62.93; H 7.11; N 6.02; S 3.42. Found: 63.0; 6.8; 5.8; 3.4.

(b₃) H-Ile-Cys(Trt)-Ser-Leu-OH 2.7 g (2.94 mmoles) of Ddz-Ile-Cys(Trt)-Ser-Leu-OH are dissolved in 52 ml of a 5 percent strength trifluoroacetic acid/methylene chloride solution containing 1% of water, and the mixture is stirred for 4 hours at room temperature. It is then neutralized with 3 ml of pyridine and the solution is concentrated in vacuo. The residue is triturated with water, filtered off, washed with water and dried over $P_2O_5$. For further purification, the substance is twice extracted by boiling with 30 ml of ethyl acetate at a time, and is each time filtered off hot.

Yield 1.51 g (70%).

$[\alpha]_D^{22} = +3.7°$ (c=1, in 90 percent strength acetic acid).

$C_{37}H_{48}N_4O_6S.0.3 CF_3COOH.1.5 H_2O$ (738.1)

Calculated: C 61.18; H 7.00; N 7.59; $CF_3COOH$ 4.63. Found: 61.0; 7.0; 7.7; 4.7.

EXAMPLE 6:

(a)
H-Ile-Cys-Ser-Leu-Tyr-Gln-Leu-Glu-Asn-Tyr-Cys-Asn-OH 3.429 g (1.5 mmoles) of H-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ trifluoroacetate are dissolved in a mixture of 19 ml of ethylmercaptan and 19 ml of trifluoroacetic acid. The reaction mixture is stirred for 4 hours at room temperature and is then poured into 250 ml of water, while stirring. The precipitate is filtered off, washed with ether and dried. It is then triturated with ether, filtered off and dried. Yield 1.964 g. This substance is then deblocked once more as described above. Yield 1.6 g (61%). In total, a further 330 mg of substance was obtainable from the filtrates after extraction with ether and freeze-drying.

Total yield: 1.93 g (73%).

$C_{63}H_{95}N_{15}O_{21}S_2.CF_3COOH.10 H_2O$ (1756.9). Calculated: C 44.43; H 6.65; N 11.96; S 3.65. Found: 44.1; 6.0; 11.6; 4.3.

The NMR spectrum does not show any Bu$^t$ signals and only a trace (about 5%) of the triphenylmethyl signal. The 18 protons of the methyl signals of isoleucine and of the two leucines at δ=0.7-1.0 are in the correct ratio to the 8 aromatic protons of the tyrosines at δ=6.5-7.1 ppm.

(b) Preparation of the starting substance H-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ trifluoroacetate (b₁)
Ddz-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ 3.4 g (16.4 mmoles) of DCCI are added at 0° C. to a solution of 22.8 g (14 mmoles) of H-Tyr(Bu$^t$)-Gln-Leu-Glu(OBu$^t$)-Asn-Tyr(Bu$^t$)-Cys(Trt)-Asn-OBu$^t$, 14.1 g (15.4 mmoles) of Ddz-Ile-Cys(Trt)-Ser-Leu-OH.1 H₂O, 2.08 g (15.4 mmoles) of HOBt and 1.8 ml (14 mmoles) of N-ethylmorpholine in 70 ml of dimethylformamide. The mixture is stirred for 1 hour at 0° C. and 3 hours at room temperature and is then left to stand overnight at room temperature, and the precipitate is filtered off. The filtrate is concentrated in vacuo and the residue is successively triturated with NaHCO₃ solution, citrate buffer (pH 3), NaHCO₃ solution and water and is filtered off in each case. It is dried over $P_2O_5$.

Yield 33.18 g (99%).

For further purification, the dry substance is suspended in 300 ml of warm ethyl acetate and the suspension is briefly heated on a steam bath. After adding 300 ml of ether, the mixture is filtered while still warm. The residue is rinsed with ether and dried in a high vacuum.

Yield 28.1 g (84%), melting point 265°-270° (with decomposition).

$[\alpha]_D^{22} = -20.3°$ (c=1, in dimethylformamide).

The product is then heated with 100 ml of methanol and after standing overnight in a refrigerator is filtered off and dried.

Yield 23.75 g (71%).

$[\alpha]_D^{22} = -25.4°$ (c=1, in dimethylformamide).

$C_{129}H_{169}N_{15}O_{25}S_2$ (2394.0)

| Amino acid analysis: | Asp | Ser | Glu | Cys | Ile | Leu | Tyr |
|---|---|---|---|---|---|---|---|
| Calculated: | 2 | 1 | 2 | 2 | 1 | 2 | 2 |
| Found: | 2.10 | 0.95 | 1.77 | 0.49 | 0.83 | 2.10 | 1.98 |

(b₂)
H-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ trifluoroacetate 24 g (about 30 mmoles) of Ddz-Ile-Cys(Trt)-Ser-Leu-Tyr(Bu$^t$)-Gln-Leu-Glu(Bu$^t$)-Asn-Tyr(Bu$^t$)-Cys(Trt)-Asn-OBu$^t$ are dissolved, whilst stirring, in a mixture of 8.75 ml (100 mmoles) of trifluoroacetic acid, 1.75 ml of water and 165 ml of methylene chloride (=about 175 ml of a 5% strength trifluoroacetic acid/methylene chloride solution containing 1% of water) and 17.5 ml of anisole. The mixture is stirred for 4 hours at room temperature. 10 ml (124 mmoles) of pyridine are then added and the mixture is concentrated. The residue is triturated with ether, filtered off, washed with ether and dried in vacuo. The substance is then triturated with water, filtered off, washed with water and dried over $P_2O_5$.

For further purification, the substance is boiled twice with 100 ml of ethyl acetate at a time and is in each case filtered off hot.

Yield 22.7 g (99%), melting point 234° (with decomposition).

$[\alpha]_D^{26} = -11.7°$ (c=1, in dimethylformamide).

$C_{117}H_{155}N_{15}O_{21}S_2 \cdot CF_3COOH$ (2285.8)

| Amino acid analysis: | Asp | Ser | Glu | Cys | Ile | Leu | Tyr |
|---|---|---|---|---|---|---|---|
| Calculated: | 2 | 1 | 2 | 2 | 1 | 2 | 2 |
| Found: | 2.05 | 0.99 | 1.88 | 0.43 | 0.73 | 2.12 | 2.05 |

EXAMPLE 7:

(a) H-Cys-Cys-Thr-Ser-OH trifluoroacetate 615.8 mg (0.5 mmole) of Ddz-Cys(Trt)-Cys(Trt)-Thr(Bu$^t$)-Ser(Bu$^t$)-OH are dissolved in a mixture of 2.5 ml of ethylmercaptan and 2.5 ml of trifluoroacetic acid. The reaction mixture is stirred for 4 hours at room temperature and is then poured into 50 ml of water. The aqueous phase is extracted three times with ether and is then freeze-dried.

Yield 240 mg (88%), $[\alpha]_D^{24} = -24.3°$ (c=1, in water).

$C_{13}H_{24}N_4O_7S_2 \cdot CF_3COOH \cdot H_2O$ (544.5) Calculated: C 33.08; H 5.00; N 10.29; S 11.77. Found: 34.4; 5.1; 10.0; 11.1.

(b) Preparation of the starting substance Ddz-Cys(Trt)-Cys(Trt)-Thr(Bu$^t$)-Ser(Bu$^t$)-OH

(b₁) Z-Thr(Bu$^t$)-Ser(Bu$^t$)-OH 12.8 ml (0.1 mole) of N-ethylmorpholine and 40.6 g (0.1 mole) of Z-Thr(Bu$^t$)-OSu (Hoppe Seyler's Z. Physiol. Chem. 346, 60 (1966)) are added at 0° C. to a suspension of 16.1 g (0.1 mole) of H-Ser(Bu$^t$)-OH (Chem. Ber. 97, 2490 (1964)) in 100 ml of dimethylformamide. The mixture is then stirred for 5 hours at room temperature and is left to stand overnight at room temperature. The product is checked for the presence of H-Ser(Bu$^t$)-OH by thin layer chromatography. If no H-Ser(Bu$^t$)-OH is detectable by this method, any undissolved matter is filtered off. The filtrate is concentrated and the residue is partitioned between ether and 110 ml of 1 N citric acid. The ether phase is washed once more with 100 ml of 0.5 N citric acid and then with water or NaCl solution until neutral. The ether phase is then dried over $Na_2SO_4$ and is concentrated, and the product is dried in a high vacuum. Yield 32.5 g of an amorphous product (72%).

$[\alpha]_D^{22} = +24.1°$ (c=1, in methanol)

$C_{22}H_{36}N_2O_7$ (452.55) Calculated: C 61.04; H 8.02; N 6.19. Found: 60.3; 7.4; 6.2.

(b₂) H-Thr(Bu$^t$)-Ser(Bu$^t$)-OH.HCl 25 g (55.24 mmoles) of Z-Thr(Bu$^t$)-Ser(Bu$^t$)-OH are dissolved in 200 ml of methanol and are hydrogenated catalytically (at pH 4.5) using an autotitrator, with addition of a solution of HCl in methanol. After completion of the hydrogenation, the Pd/BaSO₄ catalyst is filtered off, the filtrate is concentrated and the residue is dried in a high vacuum. Yield 1.1 g of an amorphous product (19.6 g=100%), $[\alpha]_D^{27} = +27°$ (c=1, in methanol)

$C_{15}H_{31}N_2O_5Cl$ (354.9)

Calculated: C 50.77; H 8.80; N 7.89. Found: 50.9; 8.8; 7.8.

(b₃) Ddz-Cys(Trt)-OH 28 ml (0.2 mole) of triethylamine and 26.5 g (0.1 mole) of Ddz-azide are added to a suspension of 36.4 g (0.1 mole) of H-Cys(Trt)-OH (J. Org. Chem. 30, 1340 (1965)) in 200 ml of dimethylformamide. The mixture is stirred for 24 hours at 40° C. The solution is then concentrated and the residue is partitioned between 100 ml of ice-cooled 1 N citric acid and ethyl acetate. The ethyl acetate phase is extracted by shaking with citric buffer (pH 3) and NaCl solution, dried over $Na_2SO_4$ and concentrated. The residue is dried in a high vacuum. Yield 37.6 g of an amorphous product (64%).

$[\alpha]_D^{22} = +27.0°$ (c=1, in methanol)

$C_{34}H_{35}NO_6S$ (585.7)

Calculated: C 69.72; H 6.02; N 2.39. Found: 69.3; 6.3; 2.6.

(b₄) Ddz-Cys(Trt)-OTcp 2.3 g of DCC, dissolved in 15 ml of tetrahydrofuran, are added at 0° C. to a solution of 5.9 g (about 10 mmoles) of Ddz-Cys(Trt)-OH and 2.2 g (11 mmoles) of 2,4,5-trichlorophenol in 50 ml of absolute tetrahydrofuran, and the mixture is stirred for 2 hours at 0° C. and is then left to stand overnight at room temperature. The DC-urea is filtered off and the solution is concentrated. The residue is dissolved in methylene chloride and the solution is filtered through 100 g of Kieselgel (silica gel) 60. Elution is carried out with methylene chloride. Yield 6.2 g of an amorphous product (81%).

$[\alpha]_D^{22} = +10.3°$ (c=1, in methanol).

$C_{40}H_{36}Cl_3NO_6S$ (765.17)

Calculated: C 62.79; H 4.74; N 1.83; S 4.19. Found: 61.0; 4.7; 1.7; 4.2.

According to CHN analysis, the substance appeared to be 97% pure.

(b₅) Ddz-Cys(Trt)-Thr(Bu$^t$)-Ser(Bu$^t$)-OH 12.8 ml (0.1 mole) of N-ethylmorpholine and 76.5 g (0.1 mole) of Ddz-Cys(Trt)-OTcp are added at 0° C. to a solution of 31.8 g (0.1 mole) of H-Thr(Bu$^t$)-Ser(Bu$^t$)-OH (or correspondingly more, depending on the water content or acid content) and 13.5 g of HOBt (0.1 mole) in 100 ml of dimethylformamide. The solution is then stirred for about 6 hours at room temperature, after which it is concentrated in a high vacuum. The residue is partitioned between ice-water and ethyl acetate. The ethyl acetate phase is extracted by shaking with NaHCO₃ solution, whereupon Ddz-Cys(Trt)-Thr(Bu$^t$)-Ser(Bu$^t$)-OH remains as the sodium salt in the ethyl acetate phase. The latter is then extracted by shaking at 0° C. with 100 ml of 1 N citric acid and 100 ml of citrate buffer (pH 3), after which it is washed neutral with water. The ethyl acetate phase is dried over $Na_2SO_4$ and is concentrated, and the residue is dried in a high vacuum. For further purification, the substance is reprecipitated from ether/petroleum ether, the ether solution being slowly added dropwise to the petroleum ether. Yield 44.5 g (50%). Melting point 116°-128° (with decomposition).

$[\alpha]_D^{22} = +25.5°$ (c=1, in methanol)

$C_{49}H_{63}N_3O_{10}S$ (886.13)

Calculated: C 66.42; H 7.17; N 4.74. Found: 66.1; 7.4; 4.7.

(b₆) H-Cys(Trt)-Thr(Buᵗ)-Ser(Buᵗ)-OH trifluoroacetate 8.8 g (10 mmoles) of Ddz-Cys(Trt)-Thr(Buᵗ)-Ser(Buᵗ)-OH are dissolved at room temperature in a mixture of 8.75 ml (0.1 mole) of trifluoroacetic acid, 1.75 ml of water and 165 ml of methylene chloride (=about 175 ml of a 5% strength solution of trifluoroacetic acid in methylene chloride, containing 1% of water). The mixture is left to stand at room temperature for 1.5 hours and is then neutralized with 8.85 ml (0.11 mole) of pyridine. The solution is concentrated and the residue is partitioned between ethyl acetate and water. The ethyl acetate phase is washed twice more with water and is dried over $Na_2SO_4$ and concentrated. The residue is dissolved in a small amount of ether and the solution is slowly added dropwise to petroleum ether.

Yield 4.2 g (54%).
Melting point 85°–95° (with decomposition).
$[\alpha]_D^{22} = +68.5°$ (c=1, in methanol)
$C_{37}H_{49}N_3O_6S \cdot CF_3COOH$ (777.9) Calculated: C 60.21; H 6.48; N 5.40; S 4.12. Found: 60.7; 6.7; 5.2; 4.2.

(b₇) Ddz-Cys(Trt)-Cys(Trt)-Thr(Buᵗ)-Ser(Buᵗ)-OH 0.9 ml (0.7 mmole) of N-ethyl-morpholine and 5.35 g (7 mmoles) of Ddz-Cys(Trt)OTcp are added at 0° to a solution of 5.3 g (6.8 mmoles) of H-Cys(Trt)-Thr(Buᵗ)-Ser(Buᵗ)-OH trifluoroacetate and 0.95 g (0.7 mmole) of HOBt in 15 ml of dimethylformamide. This solution is stirred for 14 hours at room temperature and is concentrated when the tripeptide has finished reacting. (Should unreacted tripeptide still be detectable, a little more Ddz-Cys(Trt)-OTcp has to be added). The residue is taken up in ethyl acetate. The ethyl acetate phase is washed successively with 10–20 ml of saturated NaHCO₃ solution, with 7 ml of 1 N citric acid, with 10 ml of citrate buffer and with NaCl solution until neutral, and is dried over Na₂SO₄ and concentrated. The residue is triturated with petroleum ether.

For further purification, the product is precipitated from ether/petroleum ether or is stirred with diisopropyl ether. It can also be reprecipitated from methanol/water.

Yield 6 g (71%).
Melting point 118°–130° (with decomposition).
$[\alpha]_D^{22} = +11.6°$ (c=1, in methanol)
$C_{71}H_{82}N_4O_{11}S_2$ (1231.6) Calculated: C 69.23; H 6.71; N 4.55; S 5.21. Found: 67.2; 6.3; 4.1; 5.3.

According to CHN analysis, the substance is only about 97% pure.

EXAMPLE 8

(a)

H-Cys(SO₃H)-Cys(SO₃H)-Thr-Ser-Ile-Cys(SO₃H)-Ser-Leu-Tyr-Gln-Leu-Glu-Asn-Tyr-Cys(SO₃H)-Asn-OH 983 mg (0.34 mmole) of H-Cys(Trt)-Cys(Trt)-Thr(Buᵗ)-Ser(Buᵗ)-Ile-Cys(Trt)-Ser-Leu-Tyr(Buᵗ)-Gln-Leu-Glu(OBuᵗ)-Asn-Tyr(Buᵗ)-Cys(Trt)-Asn-OBuᵗ trifluoroacetate are dissolved in a mixture of 7.5 ml of ethylmercaptan and 7.5 ml of trifluoroacetic acid. The reaction mixture is stirred for 4 hours at room temperature and is then poured into 50 ml of diethyl ether. A precipitate forms and is filtered off. The filter residue is washed with ether and dried. Yield 541 mg.

Since a slight trityl signal was still visible in the NMR spectrum, the deblocking was repeated once more with 420 mg of the substance obtained above. Yield 506.7 mg. For better characterization, the SH-peptide was converted into the S-tetrasulfonate as follows: 450 mg of the above substance are suspended in 19.6 ml of tris-HCl buffer (0.1 M, pH 7.19). After adding 9.16 g of urea, the mixture is stirred for 10 minutes and 621 mg of sodium sulfite and 621 mg of sodium tetrathionate are added at room temperature. A clear solution results. After a reaction time of 3 hours at room temperature, the mixture is placed in a refrigerator (at 4° C.) overnight. On the following day, the batch is dialyzed against 5 times 5 liters of water and is then freeze-dried.

Yield 438.9 mg (about 51%, relative to protected peptide and protein content).

$[\alpha]_D^{26} = -51°$ (c=1, in water)

The NMR spectrum shows no signal of trityl protons. In acid electrophoresis, the tetrasulfonate migrates as a single substance and somewhat more rapidly than the corresponding tetrasulfonate of the human insulin-A chain.

$C_{76}H_{117}N_{19}O_{39}S_8$ (2177.5)

| Amino acid analysis: | Asp | Thr | Ser | Glu | Cys | Ile* | Leu | Tyr |
|---|---|---|---|---|---|---|---|---|
| Calculated | 2 | 1 | 2 | 2 | 4 | 1 | 2 | 2 |
| Found | 2.00 | 0.96 | 1.76 | 1.88 | 2.73 | 1.17 | 2.27 | 1.98 |

*26.5% thereof are D-allo-Ile.

According to amino acid analysis, the peptide has a protein content of about 69%.

(b) Preparation of the starting substance
H-Cys(Trt)-Cys(Trt)-Thr(Buᵗ)-Ser(Buᵗ)-Ile-Cys(Trt)-Ser-Leu-Tyr(Buᵗ)-Gln-Leu-Glu(OBuᵗ)-Asn-Tyr(Buᵗ)-Cys(Trt)-Asn-OBuᵗ trifluoroacetate (b₁)
Ddz-Cys(Trt)-Cys(Trt)-Thr(Buᵗ)-Ser(Buᵗ)-Ile-Cys(Trt)-Ser-Leu-Tyr(Buᵗ)-Gln-Leu-Glu(OBuᵗ)-Asn-Tyr(Buᵗ)-Cys(Trt)-Asn-OBuᵗ

1.7 g (8.25 mmoles) of DCC are added at 0° C. to a solution of 16 g (7 mmoles) of H-Ile-Cys(Trt)-Ser-Leu-Tyr(Buᵗ)-Gln-Leu-Glu(OBuᵗ)-Asn-Cys-Tyr(Buᵗ)-Cys(Trt)-Asn-OBuᵗ trifluoroacetate, 9.5 g (7.7 mmoles) of Ddz-Cys(Trt)-Cys(Trt)-Thr(Buᵗ)-Ser(Buᵗ)-OH, 1.04 g (7.7 mmoles) of HOBt and 0.9 ml (7 mmoles) of N-ethylmorpholine in 70 ml of a 1:1 dimethylformamide/dimethylacetamide mixture. The batch is stirred for 2 hours at 0° C. and then at room temperature. It is left to stand overnight and on the following day is stirred for a further 5 hours at room temperature. The DC-urea which has precipitated is filtered off. The filtrate is concentrated to half its volume in a high vacuum and is then added dropwise to ice water, while stirring. The precipitate is filtered off, washed successively with NaHCO₃ solution, citrate buffer (pH 3), NaHCO₃ solution and water, and dried over P₂O₅. For further purification, the product is stirred with 100 ml of ethyl acetate, while warming. After adding 200 ml of ether, the precipitate is filtered off while still warm and is dried. The substance is then heated with 220 ml of 50 percent strength aqueous methanol and finally with 200 ml of methanol, and is in each case filtered off hot. Yield 19.42 g (81%), melting point 250°–260° (with decomposition).

$[\alpha]_D^{22} = -14.2°$ (c=1, in dimethylformamide).

$C_{188}H_{235}N_{19}O_{31}S_4 \cdot 2H_2O$ (3421.4) Calculated: C 66.00; H 7.04; N 7.78; S 3.75. Found: 65.4; 7.1; 8.0; 3.8.

Amino acid analysis (after oxidation of cystein to cysteic acid):

| | Asp | Thr | Ser | Glu | Cys | Ile | Leu | Tyr |
|---|---|---|---|---|---|---|---|---|
| Calculated: | 2 | 1 | 2 | 2 | 4 | 1 | 2 | 2 |
| Found: | 1.99 | 0.89 | 1.69 | 1.92 | 3.97 | 0.87 | 2.07 | — |

Tyrosine is absent since it is destroyed during the oxidation.

(b$_2$)
H-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ trifluoroacetate 10.26 g (3 mmoles) of Ddz-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ are dissolved, while stirring, in a mixture of 5.25 ml (60 mmoles) of trifluoroacetic acid, 1.05 ml of water and 99 ml of methylene chloride (=about 105 ml of a 5 percent strength trifluoroacetic acid/methylene chloride solution containing 1% of water) and 10.5 ml of anisole. The mixture is stirred for 4 hours at room temperature. 10.5 ml of pyridine are then added and the mixture is concentrated. Remaining volatile material is distilled off in a high vacuum. The oily residue is triturated with ether and the precipitate is filtered off and dried. The substance is then washed with water and dried over P$_2$O$_5$. For further purification, the substance is boiled three times with 10 ml of ethyl acetate at a time and is in each case filtered off hot.

Yield 7.96 g (81%), melting point 240°–245° (with decomposition).
$[\alpha]_D^{23} = -10.0°$ (c=1, in dimethylformamide).
C$_{176}$H$_{221}$N$_{19}$O$_{27}$S$_4$·CF$_3$COOH (3277.15)

| Amino acid analysis: | Asp | Thr | Ser | Glu | Cys | Ile | Leu | Tyr |
|---|---|---|---|---|---|---|---|---|
| Calculated: | 2 | 1 | 2 | 2 | 4 | 1 | 2 | 2 |
| Found: | 1.96 | 0.80 | 1.49 | 2.03 | 3.21 | 1.10 | 2.04 | 1.78 |

EXAMPLE 9

(a)
H-Gly-Ile-Val-Glu-Gln-Cys(SO$_3$H)-Cys(SO$_3$H)-Thr-Ser-Ile-Cys(SO$_3$H)-Ser-Leu-Tyr-Gln-Leu-Glu-Asn-Tyr-Cys(SO$_3$H)-Asn-OH (=human insulin-A chain tetrasulfonate)

772 mg (0.2 mmole) of H-Gly-Ile-Val-Glu(OBu$^t$)-Gln-Cys(Trt)-Cys(Trt)-Thr(Bu$^t$)-Ser(Bu$^t$)-Ile-Cys(Trt)-Ser-Leu-Tyr-Bu$^t$)-Gln-Leu-Glu(OBu$^t$)-Asn-Tyr(Bu$^t$)-Cys(Trt)-Asn-Obu$^t$. CF$_3$COOH are suspended in a mixture of 5 ml of ethylmercaptan and 5 ml of trifluoroacetic acid. The mixture is stirred for 4 hours at room temperature and poured into 50 ml of ether. The precipitate formed is filtered off and washed with ether. Yield 542 mg. This operation was repeated with the 542 mg of substance. Yield 385.9 mg. The protein content is 80%, so that this yield corresponds to about 65%.

C$_{99}$H$_{155}$N$_{25}$O$_{35}$S$_4$ (2383.8).

To characterize the substance, 360 mg thereof were used to prepare the tetrasulfonate analogously to Example 8a. Yield 370.8 mg (about 60%, relative to protected insulin-A chain).
$[\alpha]_D^{21} = -72.9°$ (c=1, in water)
C$_{99}$H$_{155}$N$_{25}$O$_{47}$S$_8$ (2704)

| Amino acid analysis: | Asp | Thr | Ser | Glu | Gly | Cys | Val | Ile | Leu | Tyr |
|---|---|---|---|---|---|---|---|---|---|---|
| Calculated: | 2 | 1 | 2 | 4 | 1 | 4 | 1 | 2 | 2 | 2 |
| Found: | 1.84 | 0.90 | 1.62 | 4.04 | 0.94 | 3.48 | 0.89 | 1.81* | 2.2 | 2.2 |

*Sum of 0.44 D-allo-Ile and 1.37 Ile (b) Preparation of the starting substance
H-Gly-Ile-Val-Glu(OBu$^t$)-Gln-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)Cys-(Trt)-Asn-OBu$^t$.
CF$_3$COOH (b$_1$) Ddz-Val-OTcp A solution of 72.1 g (0.35 mmole) of DCC in 100 ml of ethyl acetate is added at 0° C. to a solution of 113.3 g (0.334 mmole) of Ddz-Val-OH and 65.9 g (0.334 mmole) of 2,4,5-trichlorophenol in 300 ml of ethyl acetate. The mixture is stirred for 1 hour at 0° and for 3 hours at room temperature. The DC-urea is filtered off and the filtrate is concentrated. The residue is caused to crystallize by means of petroleum ether.

Yield 111.45 g (64%), melting point 73°–76°,
$[\alpha]_D^{25} = -28.7°$ (c=1, in methanol)
C$_{23}$H$_{26}$NO$_6$Cl$_3$ (518.84) Calculated: C 53.24; H 5.05; N 2.70. Found: 53.5; 5.2; 2.9.

(b$_2$) Ddz-Val-Glu(OBu$^t$)-OH 19.2 ml (150 mmoles) of N-ethylmorpholine and 77.8 g of Ddz-Val-OTcp are added to a solution of 30.5 g (150 mmoles) of H-Glu(OBu$^t$)-OH and 20.25 g (150 mmoles) of HOBt in 200 ml of dimethylformamide. The mixture is stirred for 4 hours at room temperature. When H-Glu(OBu$^t$)-OH is no longer detectable in a thin layer chromatogram, the mixture is concentrated in a high vacuum. (If some is still detectable, the reaction is completed by adding a small amount of Ddz-Val-OTcp). The resulting oil is partitioned between 300 ml of ethyl acetate and 300 ml of water. The ethyl acetate phase is extracted by shaking twice with 150 ml portions of citrate buffer (pH 3) at a time and once with 150 ml of water and is dried over Na$_2$SO$_4$ and concentrated. Yield 138.7 g (78.7 g$\stackrel{\wedge}{=}$100%). The resulting oil is reacted further without additional purification and characterization, and is taken to be 150 mmoles.
C$_{26}$H$_{40}$N$_2$O$_9$ (524.6).

(b$_3$) Ddz-Val-Glu(OBu$^t$)-Gln-ONb 19.2 ml (150 mmoles) of N-ethylmorpholine and 33 g (160 mmoles) of DCC are added, at 0° C., to a solution of 138.7 g (=150 mmoles) of crude, impure Ddz-Val-Glu(OBu$^t$)-OH, 47.65 g (150 mmoles) of H-Gln-ONb. HCl and 20.25 g (150 mmoles) of HOBt in 450 ml of dimethylformamide. The mixture is stirred for 1 hour at 0° C. and for 4 hours at room temperature. It is then left to stand overnight at room temperature, the precipitate is filtered off and the filtrate is concentrated in a high vacuum. The resulting oil is partitioned between 300 ml of ethyl acetate and 300 ml of water. The ethyl acetate phase is successively extracted by shaking with saturated NaHCO$_3$ solution, citrate buffer (pH 3), saturated NaHCO$_3$ solution and water, and is dried over Na$_2$SO$_4$ and concentrated. The oil crystallizes on treatment with ether. The product is washed with ether.

Yield 110.95 g (94%), melting point 135°–138°, 138°–142°.

$[\alpha]_D^{22} = -49.4°$ (c=1, in methanol).

C$_{38}$H$_{53}$N$_5$O$_{13}$ (787.9) Calculated: C 57.93; H 6.78; N 8.89. Found: 57.8; 7.0; 9.2.

(b$_4$) H-Val-Glu-(OBu$^t$)-Gln-ONb trifluoroacetate 39.4 g (50 mmoles) of Ddz-Val-Glu(OBu$^t$)-Gln-ONb are dissolved in a mixture of 875 ml of a 5% strength trifluoroacetic acid/methylene chloride mixture (containing 1% of water) (=500 mmoles of trifluoroacetic acid) and 87.5 ml of anisole. The mixture is left to stand at room temperature for 30 minutes and is then neutralized with 50 ml of pyridine and concentrated. The residue is finally dried in a high vacuum, after which it is partitioned between ethyl acetate and water. The ethyl acetate phase is additionally extracted by shaking twice with a small amount of water, and is dried over Na$_2$SO$_4$ and concentrated. The residue is triturated with ether and dried in a high vacuum. Yield 23.6 g of an amorphous substance (69%).

$[\alpha]_D^{24} = -5.3°$ (c=1, in methanol).

C$_{26}$H$_{39}$N$_5$O$_9$·CF$_3$COOH (679.67) Calculated: C 49.48; H 5.93; N 10.30. Found: 50.0; 5.8; 10.1.

(b$_5$) Ddz-Gly-Ile-OMe

To a solution of 14.54 g (80 mmoles) of H-Ile-OMe·HCl and 10.8 g (80 mmoles) of HOBt in 50 ml of dimethylformamide are added 10.3 ml (80 mmoles) of N-ethylmorpholine at −3° C. and 40 g (84 mmoles) of Ddz-Gly-OTcp at 0° C. The mixture is stirred for 3 hours at room temperature and is then left to stand overnight. (On the following day, some H-Ile-OMe was still detectable in a thin layer chromatogram. For this reason, a further 2.86 g (6 mmoles) of Ddz-Gly-OTcp were added and the mixture was stirred. After 5 hours, no H-Ile-OMe was detectable).

The solution, which in a thin layer chromatogram is free from H-Ile-OMe, is concentrated in a high vacuum and the resulting oil is partitioned between ethyl acetate and water. The ethyl acetate solution is washed successively with saturated NaHCO$_3$ solution, citrate buffer (pH 3), NaHCO$_3$ solution and water and is dried over Na$_2$SO$_4$. It is then filtered over 400 g of basic Al$_2$O$_3$, the eluate is concentrated and the residue is dried in a high vacuum. Yield 30.6 g of a viscous oil (90%).

$[\alpha]_D^{25} = -6.8°$ (c=1, in methanol).

C$_{21}$H$_{32}$N$_2$O$_7$ (424.5) Calculated: C 59.42; H 7.60; N 6.60. Found: 59.1; 7.7; 6.3.

(b$_6$) Ddz-Gly-Ile-OH 10 g (23.56 mmoles) of Ddz-Gly-Ile-OMe are dissolved in a mixture of 24 ml of dioxane and 8 ml of water and are titrated with 1 N NaOH against thymolphthalein as the indicator. The consumption depends on the ethyl acetate content but is more than 23 ml. After neutralization with citric acid, the dioxane is distilled off. The residue is taken up in water and brought to pH 3 with 2 N citric acid at 0° C. The oil which precipitates is extracted with ethyl acetate. The aqueous phase is again acidified to pH 3 if necessary and is extracted with ethyl acetate. The combined ethyl acetate extracts are extracted by shaking once with water, dried over Na$_2$SO$_4$ and concentrated. The residue is dried in a high vacuum. The substance becomes amorphous.

Yield 8.9 g (92%). Melting point 80°–90°.

$[\alpha]_D^{23} = +4.2°$ (c=1, in methanol).

C$_{20}$H$_{30}$N$_2$O$_7$ (410.48) Calculated: C 58.52; H 7.37; N 6.83. Found: 58.8; 7.5; 6.5.

(b$_7$) Ddz-Gly-Ile-Val-Glu(OBu$^t$)-Gln-ONb 4.48 ml (35 mmoles) of N-ethylmorpholine and 8.47 g (41 mmoles) of DCC are added at 0° C. to a solution of 15.8 g (38.5 mmoles) of Ddz-Gly-Ile-OH, 23.8 g (35 mmoles) of H-Val-Glu(OBu$^t$)-Gln-ONb trifluoroacetate and 5.2 g (38.5 mmoles) of HOBt in 60 ml of dimethylformamide. The mixture is stirred for one hour at 0° C. and then for several hours at room temperature, after which it is left to stand overnight at room temperature. A gel forms, which is stirred into cooled NaHCO$_3$ solution. The product is filtered off and is successively triturated with citrate buffer (pH 3), NaHCO$_3$ solution and water and is filtered off after each trituration. It is then dried over P$_2$O$_5$. Yield 40.3 g.

For further purification, the product is recrystallized from 500 ml of ethanol. Yield 21.45 g (64%), melting point 205°–207°.

$[\alpha]_D^{25} = -12.3°$ (c=1, in dimethylformamide).

A smaller batch, giving a lower yield, exhibited the following data: melting point 212°–214°, $[\alpha]_D^{25} = -16.1°$ (c=1, in dimethylformamide).

C$_{46}$H$_{67}$N$_7$O$_{15}$ (958.1) Calculated: C 57.57; H 7.05; N 10.23. Found: 57.6; 7.2; 10.0.

(b$_8$) Ddz-Gly-Ile-Val-Glu(OBu$^t$)-Gln-OH 19.16 g (20 mmoles) of Ddz-Gly-Ile-Val-Glu(OBu$^t$)Gln-ONB are dissolved in a mixture of 100 ml of dimethylformamide and 100 ml of methanol. After adding Pd/BaSO$_4$, the mixture is catalytically hydrogenated. After 6 hours, hydrogenation is complete. The suspension is heated to about 70° C. and the catalyst is filtered off while warm. The residue is rinsed with warm dimethylformamide. The filtrate is concentrated and the residue is triturated with 100 ml of methanol. The mixture is left to stand overnight in a refrigerator and the product is filtered off and rinsed with cold methanol. It is then dried in vacuo over P$_2$O$_5$.

Yield 14 g (85%), melting point 238°–241° (with decomposition).

$[\alpha]_D^{29} = -13.3°$ (c=1, in dimethylformamide).

C$_{39}$H$_{62}$N$_6$O$_{13}$ (822.97) Calculated: C 56.92; H 7.59; N 10.21. Found: 56.0; 7.6; 10.8.

(b$_9$) Ddz-Gly-Ile-Val-Glu(OBu$^t$)-Gln-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ 0.13 ml of N-ethylmorpholine, followed at 0° C. by 310 mg (1.5 mmoles) of DCC, are added to a solution of 3.28 g (1 mmole) of H-Cys(Trt)-Cys(Trt)-Thr(Bu$^t$)-Ser(Bu$^t$)-Ile-Cys (Trt)-Ser-Leu-Tyr(Bu$^t$)-Gln-Leu-Glu(OBu$^t$)-Asn-Tyr(Bu$^t$)-Cys (Trt)-Asn-OBu$^t$ trifluoroacetate, 1 g (about 1.2 mmoles) of Ddz-Gly-Ile-Val-Glu(OBu$^t$)-Gln-OH and 162 mg of HOBt (1.2 mmoles) in 20 ml of a 1:1 mixture of dimethylformamide and dimethylacetamide. The mixture is stirred for 1 hour at 0° C. and 6 hours at room temperature and is then left to stand overnight. A thick gel forms, which is decomposed with ice water. The precipitate which forms is filtered off and is successively triturated with NaHCO$_3$ solution, citrate buffer (pH 3), NaHCO$_3$ solution and water, and is filtered off in each case. It is then washed with water and dried over $P_2O_5$. For further purification, it is twice boiled with 25 ml of ethyl acetate at a time, and filtered off hot. Yield 2.87 g (72%). Melting point 260°–278° (with decomposition).

$[\alpha]_D^{24} = -24.5°$ (c=1, in dimethylformamide).
$C_{215}H_{281}N_{25}O_{39}S_4$ (3968.07).

| Amino acid analysis: | Asp | Thr | Ser | Glu | Gly | Cys | Val | Ile | Leu | Tyr |
|---|---|---|---|---|---|---|---|---|---|---|
| Calculated: | 2 | 1 | 2 | 4 | 1 | 4 | 1 | 2 | 2 | 2 |
| Found: | 2.06 | 0.88 | 2.04 | 3.97 | 1.01 | 2.59 | 0.60 | 1.45 | 1.93 | 1.93 |

(b₁₀)

H-Gly-Ile-Val-Glu(OBu^t)-Gln-Cys(Trt)-Cys(Trt)-Thr(Bu^t)-Ser(Bu^t)-Ile-Cys(Trt)-Ser-Leu-Tyr(Bu^t)-Gln-Leu-Glu(OBu^t)-Asn-Tyr(Bu^t)-Cys(Trt)-Asn-OBu^t trifluoroacetate 2.78 g (0.7 mmole) of Ddz-Gly-Ile-Val-Glu(OBu^t)-Gln-Cys(Trt)-Cys(Trt)-Thr(Bu^t)-Ser(Bu^t)-Ile-Cys(Trt)-Ser-Leu-Tyr(Bu^t)-Gln-Leu-Glu(OBu^t)-Asn-Tyr(Bu^t)-Cys(Trt)-Asn-OBu^t and 2.5 ml of anisole in 25 ml of a 5 percent strength tritrifluoroacetic acid/methylene chloride solution containing 1% of water (=about 14 mmoles of trifluoroacetic acid) are stirred for 4 hours at room temperature. 1.4 ml of pyridine are then added and the mixture is first concentrated in the vacuum from a waterpump and finally in a high vacuum. The residue is triturated with ether, filtered off, washed with ether and dried. The substance is then triturated with water, filtered off, washed with water and dried over $P_2O_5$. It is further purified by boiling it twice with 50 ml of ethyl acetate at a time, and filtering off hot. Yield 1.85 g (68.5%), melting point 275°–280° (with decomposition).

$[\alpha]_D^{23} = -24.0°$ (c=1, in dimethylformamide).
$C_{203}H_{267}N_{25}O_{35}S_4 \cdot CF_3COOH$ (3859.8)

| Amino acid analysis: | Asp | Thr | Ser | Glu | Gly | Cys | Val | Ile | Leu | Tyr |
|---|---|---|---|---|---|---|---|---|---|---|
| Calculated: | 2 | 1 | 2 | 4 | 1 | 4 | 1 | 2 | 2 | 2 |
| Found: | 2.05 | 1.08 | 1.80 | 4.00 | 0.97 | 2.40 | 0.71 | 1.51 | 2.06 | 1.88 |

I claim:
1. A method for detaching the S-trityl group from an S-trityl compound of a peptide containing cysteine protected with an S-trityl group, which method comprises treating said S-trityl compound with a mixture of a mercaptan and trifluoroacetic acid.
2. A method as in claim 1 wherein said mercaptan is a member selected from the group consisting of ethyl mercaptan, mercaptoacetic acid, and thiophenol.
3. A method as in claim 1 wherein said mercaptan is ethyl mercaptan.

* * * * *